US012600745B2

(12) United States Patent
Lenna et al.

(10) Patent No.: US 12,600,745 B2
(45) Date of Patent: Apr. 14, 2026

(54) PROCESS FOR PREPARING B-[(7A, 1713)-17-HYDROXY-7-[9-[(4,4,5,5,5-PENTAFLUOROPENTYL)SULFINYL] NONYL]ESTRA-1,3,5(10)-TRIEN-3-YL]-BORONIC ACID

(71) Applicant: INDUSTRIALE CHIMICA S.R.L., Milan (IT)

(72) Inventors: Roberto Lenna, S. Giorgio su Legnano (IT); Andrea Fasana, Nesso (IT)

(73) Assignee: Industriale Chimica S.R.L., Milan (IT)

( * ) Notice: Subject to any disclaimer, the term of this patent is extended or adjusted under 35 U.S.C. 154(b) by 428 days.

(21) Appl. No.: 18/281,943

(22) PCT Filed: Mar. 29, 2022

(86) PCT No.: PCT/EP2022/058213
§ 371 (c)(1),
(2) Date: Sep. 13, 2023

(87) PCT Pub. No.: WO2022/207607
PCT Pub. Date: Oct. 6, 2022

(65) Prior Publication Data
US 2024/0174711 A1 May 30, 2024

(30) Foreign Application Priority Data
Mar. 31, 2021 (IT) ........................ 102021000008066

(51) Int. Cl.
*C07J 31/00* (2006.01)

(52) U.S. Cl.
CPC .................................. *C07J 31/006* (2013.01)

(58) Field of Classification Search
CPC ..................................................... C07J 31/006
USPC ............................................................. 540/4
See application file for complete search history.

(56) References Cited

FOREIGN PATENT DOCUMENTS

| | | | |
|---|---|---|---|
| EP | 3473630 | B1 | 1/2021 |
| WO | 9500478 | | 1/1995 |
| WO | 2016004166 | A1 | 1/2016 |
| WO | 2017192991 | A1 | 11/2017 |

OTHER PUBLICATIONS

E. J. Brazier et al., "Fulvestrant: From the Laboratory to Commercial-Scale Manufacture," Org. Process Res. Dev., 2010, vol. 14, No. 3, pp. 544-552.

J. Liu et al., "Fulvestrant-3 boronic acid (ZB716): an orally bioavailable selective estrogen receptor downregulator (SERD)", J. Med. Chem., 2016, vol. 59, pp. 8134-8140.

*Primary Examiner* — Kristin A Vajda
(74) *Attorney, Agent, or Firm* — Fish IP Law, LLP

(57) ABSTRACT

The present invention relates to a process for preparing B-[(7α,17β)-17-hydroxy-7-[9-[(4,4,5,5,5-pentafluoropentyl)sulfinyl]nonyl]estra-1,3,5(10)-trien-3-yl]-boronic acid, also known as Fulvestrant-3-boronic acid or ZB716, whose structure is reported below.

(I)

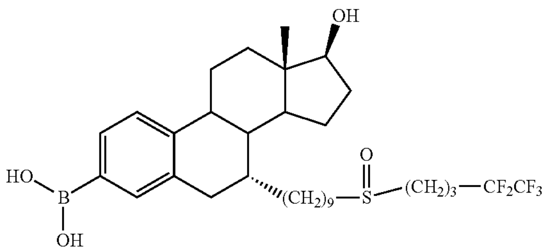

6 Claims, No Drawings

PROCESS FOR PREPARING B-[(7A, 1713)-17-HYDROXY-7-[9-[(4,4,5,5,5-PENTAFLUOROPENTYL)SULFINYL] NONYL]ESTRA-1,3,5(10)-TRIEN-3-YL]-BORONIC ACID

This application is a nationalization of International Patent Application No. PCT/EP2022/058213 filed on Mar. 29, 2022. These and all other referenced extrinsic materials are incorporated herein by reference in their entirety. Where a definition or use of a term in a reference that is incorporated by reference is inconsistent or contrary to the definition of that term provided herein, the definition of that term provided herein is deemed to be controlling.

FIELD OF THE INVENTION

The present invention relates to the sector of processes for the synthesis of active ingredients for pharmaceutical use, and in particular to a process for preparing B-[(7α,17β)-17-hydroxy-7-[9-[(4,4,5,5,5-pentafluoropentyl)sulfinyl]nonyl] estra-1,3,5(10)-trien-3-yl]-boronic acid, also known as Fulvestrant-3-boronic acid or ZB716, on an industrial scale. The compound is identified by the CAS Number 1853279-29-4.

STATE OF THE ART

ZB716 is useful for the treatment of metastatic breast cancer. The structure of the compound is shown below:

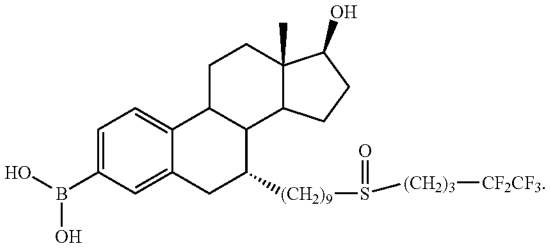

The compound is described and claimed in patent EP 3473630 B1 (Compound 29, claim 1) by Xavier University of Louisiana.

The article "Fulvestrant-3 boronic acid (ZB716): an orally bioavailable selective estrogen receptor downregulator (SERD)", J. Liu et al., J. Med. Chem. 2016, 59, 8134-8140, reports an experimental description of the preparation of the compound in question (page 8135, Scheme 1); this synthesis starts from the compound KSM, having the formula shown below:

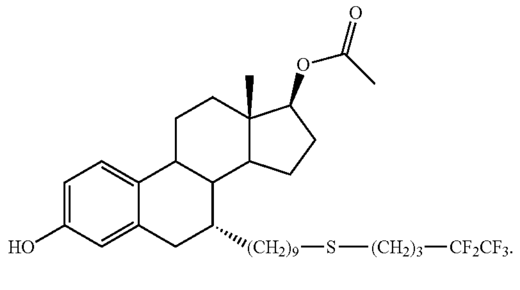

The compound KSM can in turn be obtained by following what is reported in the article "Fulvestrant: from the laboratory to commercial-scale manufacture" E. J. Brazier et al., Org. Process Res. Dev. 2010, 14, 3, 544-552, which describes the synthesis of another active ingredient, Fulvestrant, also currently used for the treatment of metastatic breast cancer.

As can be learned from J. Med. Chem. 2016, 59, 8134-8140, compound ZB716 shows apparent clinical advantages over Fulvestrant that shares with it a large portion of the structure. In the following figure the structural differences between Fulvestrant and ZB716 are highlighted:

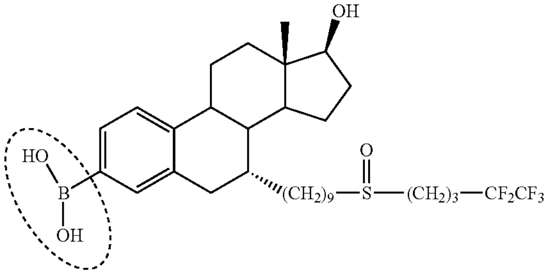

ZB716

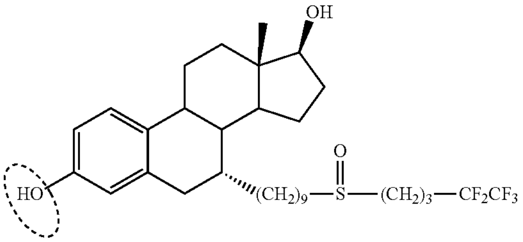

FULVESTRANT

The Applicant has been producing Fulvestrant for years but with a different process from that described in Organic Process Research & Development 2010, 14, 544-552.

This process does not involve the use of intermediate 1 by J. Med. Chem. 2016, 59, 8134-8140, having the following structural formula:

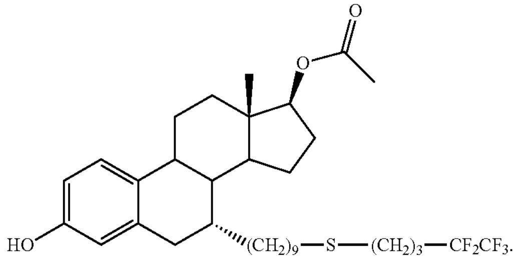

It is an object of the present invention to provide a process for the production of compound ZB716.

SUMMARY OF THE INVENTION

This object is achieved with the present invention, which relates to a process for the synthesis of ZB716 comprising the following steps:

a) reaction of intermediate N-3, (7α,17β)-7-[9-[(4,4,5,5,5-pentafluoropentyl)sulfinyl]nonyl]-estra-1,3,5(10)-triene-3,17-diol (Fulvestrant), with a triflating agent to obtain intermediate N-2, (7α,17β)-7-[9-[(4,4,5,5,5-pentafluoropentyl)sulfinyl]nonyl]-estra-1,3,5(10)-triene-3,17-diol-3-triflate:

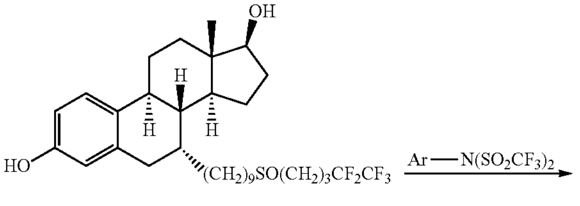

N-3

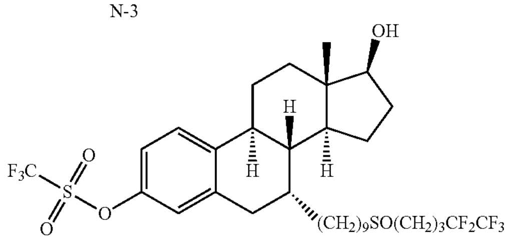

N-2 b) reaction of intermediate N-2 with 4,4,4',4',5,5,5',5'-octamethyl-2,2'-bi-1,3,2-dioxaborolane to obtain intermediate N-1, (7α,17β)-7-[9-[(4,4,5,5,5-pentafluoropentyl)sulfinyl]nonyl]-3-(4,4,5,5-tetramethyl-1,3,2-dioxaborolan-2-yl)-estra-1,3,5(10)-trien-17-ol:

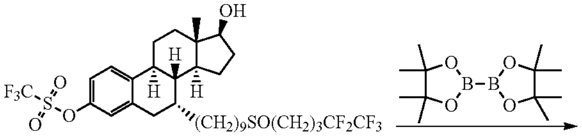

N-2

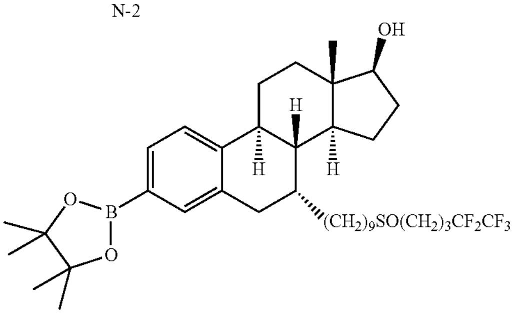

N-1 c) treatment of intermediate N-1 to obtain compound ZB716, B-[(7α,17β)-17-hydroxy-7-[9-[(4,4,5,5,5-pentafluoropentyl)sulfinyl]nonyl]estra-1,3,5(10)-trien-3-yl]-boronic acid:

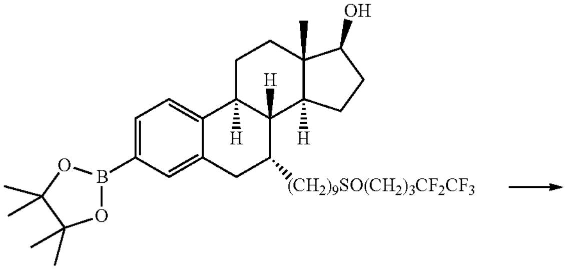

N-1

-continued

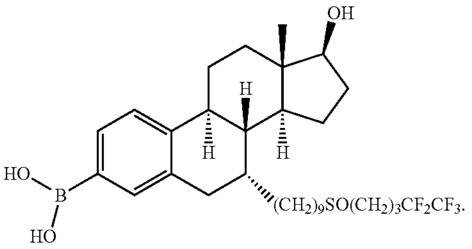

ZB716

DETAILED DESCRIPTION OF THE INVENTION

In its first aspect, the invention relates to a process for the synthesis of ZB716 comprising the steps described below.

In the description of the reactions forming the process of the invention, the ratios between reagents are indicated as w/w, i.e. ratios by weight, unless otherwise specified.

Step a) consists in the reaction of intermediate N-3, (7α,17β)-7-[9-[(4,4,5,5,5-pentafluoropentyl)sulfinyl]nonyl]-estra-1,3,5(10)-triene-3,17-diol, with a triflating agent to obtain intermediate N-2, (7α,17)-7-[9-[(4,4,5,5,5-pentafluoropentyl)sulfinyl]nonyl]-estra-1,3,5(10)-triene-3,17-diol-3-triflate:

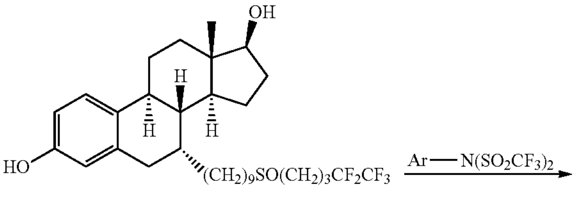

N-3

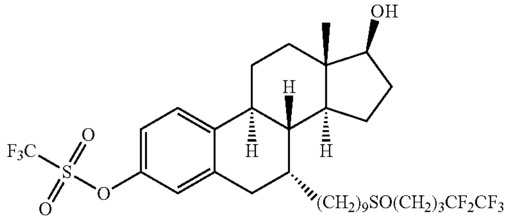

N-2

Intermediate N-3 is the compound Fulvestrant, produced by the Applicant following the process described in patent EP 2183267 B1; the process described in EP 2183267 B1 makes intermediate N-3, Fulvestrant, available with a quality suitable for use also in the process to obtain the new active ingredient ZB716.

Triflation exclusively occurs at the phenolic hydroxy group without having to protect the other hydroxy group present in the molecule, using an aromatic bis(trifluoromethanesulfonimide) of general formula Ar—$N(Tf)_2$ as triflating agent, wherein Ar indicates the aromatic or heterocyclic radical and the $N(Tf)_2$ group is the radical:

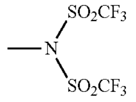

For the purposes of the present invention, the preferred triflating agent is the compound 1,1,1-trifluoro-N-phenyl-N-[(trifluoromethyl)sulfonyl]methanesulfonamide (also commonly referred to as N,N-bis (trifluoromethanesulfonyl) aniline) having the formula shown below:

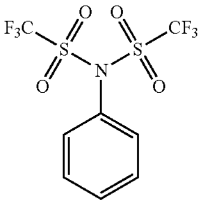 [SMILES: O=S(=O)(N(c1ccccc1)S(=O)(=O)C(F)(F)F)C(F)(F)F]

The triflating agent is used in a (w/w) ratio comprised between 0.30 and 1.20 with respect to intermediate N-3, preferably it is used in a (w/w) ratio between 0.6 and 1.0.

The reaction is carried out in dichloromethane (DCM), operating at a temperature comprised between −15 and 40° C., preferably between 0 and 30° C., for a time comprised between 4 and 12 hours, preferably between 6 and 8 hours, in the presence of an organic base selected from triethylamine, diisopropylethylamine, pyridine, 4-(dimethylamino) pyridine, 2,6-lutidine. Triethylamine is preferably used.

Step b) consists in the reaction of intermediate N-2 obtained in the previous step with 4,4,4',4',5,5,5',5'-octamethyl-2,2'-bi-1,3,2-dioxaborolane to obtain intermediate N-1, (7α,17β)-7-[9-[(4,4,5,5,5-pentafluoropentyl)sulfinyl]nonyl]-3-(4,4,5,5-tetramethyl-1,3,2-dioxaborolan-2-yl)-estra-1,3,5(10)-trien-17-ol:

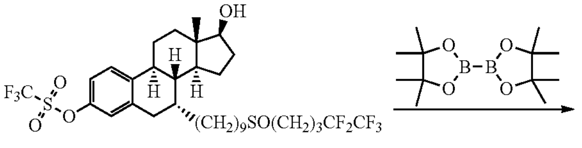

N-2

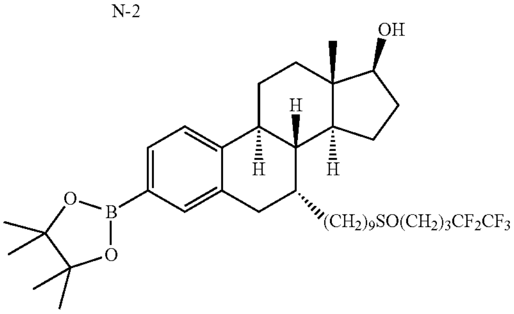

N-1

The compound 4,4,4',4',5,5,5',5'-octamethyl-2,2'-bi-1,3,2-dioxaborolane is widely commercially available and is also referred to by the common name bis(pinacolato)diboron.

Bis(pinacolato)diboron is used in a (w/w) ratio comprised between 0.11 and 0.45, preferably between 0.25 and 0.40, with respect to intermediate N-2.

The reaction is carried out in acetonitrile operating at a temperature comprised between 70 and 90° C., preferably between 75 and 85° C., for a time comprised between 1 and 6 hours, preferably between 2 and 4 hours, in the presence of an organic derivative of palladium(II) such as palladium (II) acetate, a phosphine such as tricyclohexylphosphine, and a base such as sodium or potassium acetate or sodium or potassium methylate; the preferred bases are potassium acetate and potassium methylate.

Finally, in the last step of the process, c), the intermediate N-1 is converted into the desired compound, ZB716:

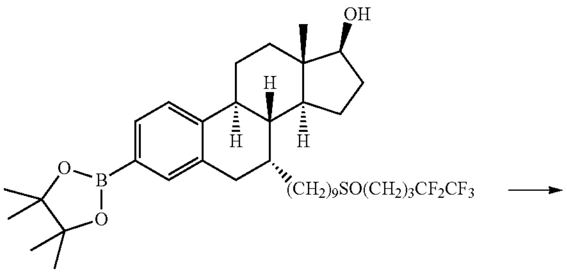

N-1

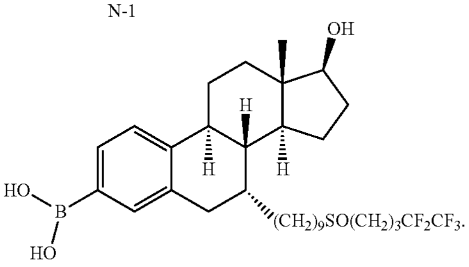

ZB716

Lithium hydroxide hydrate, potassium hydroxide and sodium hydroxide, or sodium or potassium periodate with ammonium acetate can be used as reagents.

When using a periodate, the reagent is used in a (w/w) ratio comprised between 0.3 and 2.4, preferably between 1.1 and 1.4, with respect to intermediate N-1; the use of sodium periodate is preferred over that of potassium. The required amount of reagent is precisely defined by the reaction control.

Operating with a periodate, the reaction is carried out using as solvent a mixture of water with a water miscible solvent, such as methanol, tetrahydrofuran (THF) or acetone.

Preferred reaction conditions are the use of aqueous acetone in the presence of ammonium acetate, a temperature comprised between 10 and 45° C., preferably between 20 and 30° C., and a reaction time comprised between 8 hours and 36 hours, preferably between 16 and 30 hours.

When using hydroxides, it is possible to operate using methanol or tetrahydrofuran (THF) as solvents, optionally in the presence of water.

The invention will be further illustrated by the following examples.

Instruments, Methods and Experimental Conditions

NMR:

NMR spectrometer JEOL 400 YH (400 MHz); Software JEOL Delta v5.1.1; Spectra recorded in deuterated solvents such as: Chloroform-d, D 99.8%, containing 0.1% (v/v)

tetramethylsilane (TMS) as internal standard; and Chloroform-d, "100%", D 99.96%, containing 0.03% (v/v) TMS, and DMSO-$d_6$.

MS 1:

- Instrument: DSQ-trace Thermofisher
- Sample introduction—direct exposure probe (dep)
- Chemical ionization (CI) with methane
- Methane pressure: 2.2 psi
- Source Temperature: 200° C.

MS 2:

- Instrument: Waters Acquity UPLC QDa Detector
- Electrospray ionization (ESI) with formic acid
- Source Temperature: 120° C.

UPLC:

- Chromatographic System: Waters Acquity UPLC; Detector: Acquity UPLC PDA and λ Detector
- Chromatographic Conditions:
  - Column: Acquity UPLC BEH C18 1.7 μm, 2.1×50 mm
  - Flow rate: 0.5 mL/min
  - Detector: UV 225 nm
  - Injection Volume: 1 μL
  - Temperature: 35° C.
  - Mobile phase A: $H_2O$+0.01% trifluoroacetic acid (TFA)
  - Mobile phase B: Acetonitrile+0.01% TFA

| TIME (min.) | Mobile phase A (v/v) | Mobile phase B (v/v) |
|---|---|---|
| 0.00 | 40 | 60 |
| 0.00-3.00 | 40 | 60 |
| 3.00-3.10 | 10 | 90 |
| 3.10-5.00 | 10 | 90 |
| 5.00-5.10 | 40 | 60 |
| 5.10-6.00 | 40 | 60 |

TLC

MERCK: TLC silica gel 60 $F_{254}$ Aluminium sheets 20×20 cm, cod. 1.0554.0001.

TLC Stains

Cerium phosphomolybdate: 25 g of phosphomolybdic acid and 10 g cerium (IV) sulfate are dissolved in 600 mL of $H_2O$. 60 mL of 98% $H_2SO_4$ are added and brought to 1 L with $H_2O$. The plate is impregnated with the solution and then heated until the products are detected.

Notes

The water used in the experimental descriptions is to be intended as pure water, unless otherwise indicated.

The organic solvents used in the experimental descriptions are to be intended of "technical" grade, unless otherwise indicated.

The reagents and catalysts used in the experimental descriptions are to be intended of commercial quality, unless otherwise indicated.

Example 1

This example refers to step a) of the process of the invention, from intermediate N-3, Fulvestrant, to intermediate N-2, Fulvestrant triflate.

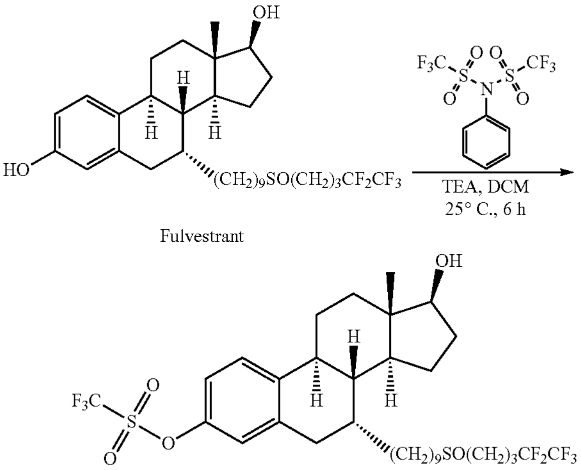

Fulvestrant

Fulvestrant triflate

A flask is charged with 5 g of Fulvestrant N-3, 70 mL of dichloromethane and 3.5 mL of triethylamine (TEA).

The mixture is cooled to 5° C., and a solution of N,N-bis(trifluoromethanesulfonyl)aniline (4.70 g) dissolved in 12 mL of dichloromethane is added dropwise in about 15 minutes. The mixture is brought to 25° C. and kept under stirring for 6 hours.

Once the reaction is complete (UPLC monitoring) the solvent is removed by distilling under reduced pressure at 45° C. to obtain 11.5 g of Fulvestrant triflate N-2 (oil) which is reacted as such in the subsequent reaction.

The Fulvestrant used as the starting reagent of the method, subjected to $^1$H-NMR and Ms analysis, shows the following analytical data:

$^1$H-NMR (400 MHz, DMSO-d6): 8.99 (s, 1H); 7.04 (d, 1H, J=8.4 Hz); 6.49 (d, 1H, J=8.0 Hz); 6.41 (s, 1H); 4.50 (s, 1H); 3.54-3.52 (m, 1H); 2.76-0.71 (m, 38H); 0.66 (s, 3H).

The $^1$H-NMR signals at 8.99 ppm and 4.50 ppm (attributable to the mobile protons in position 3 and 17) disappear after deuteration of the sample with $D_2O$.

Mass (ESI): m/z=629 [$M^+$+1+22]; 607 [$M^+$+1]; 589 [$M^+$+1−$H_2O$].

The Fulvestrant triflate obtained, subjected to $^1$H-NMR and Ms analysis, shows the following analytical data:

$^1$H-NMR (400 MHz, DMSO-d6): disappearance of Fulvestrant signal at 8.99 (s, 1H) but not of the signal at 4.50 (s, 1H) ppm (of Fulvestrant).

Mass (ESI): m/z=761 [$M^+$+1+22]; 739 [$M^+$+1]; 619 [$M^+$+1−$HCF_2CF_3$].

Example 2

This example refers to step b) of the process of the invention, synthesis of intermediate N-1 of the process of the invention starting from Fulvestrant triflate (intermediate N-2).

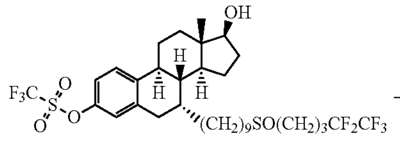

Fulvestrant triflate

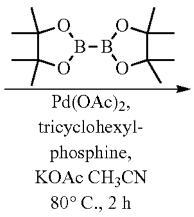

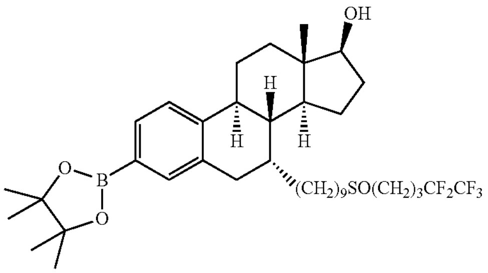

N-1

A flask is charged with the intermediate Fulvestrant triflate N-2 obtained according to the procedure described in the previous example and 160 mL of acetonitrile. The mixture is kept under stirring at 25° C. for 10 minutes. 3.1 g of bis(pinacolato)diboron, 2.2 g of potassium acetate, 0.25 g of palladium acetate and 0.49 g of tricyclohexylphosphine are added to the solution. The mixture is heated to 80° C. for 2 hours.

The reaction is monitored by UPLC analysis.

Once the reaction is complete, it is cooled to 25° C., carbon is added (0.2 g) and the mixture is filtered through a layer of dicalite (8 g). It is concentrated under reduced pressure at 45° C. until an oily residue is obtained.

The residue is suspended in 100 mL of isopropyl acetate and silica gel is added.

The suspension is kept under stirring at 25° C. for 1 hour.

The solvent is filtered and concentrated under reduced pressure at 45° C. to obtain 12.8 g of intermediate N-1.

Example 3

This example refers to the implementation of step c) of the process of the invention, from intermediate N-1 to compound ZB716:

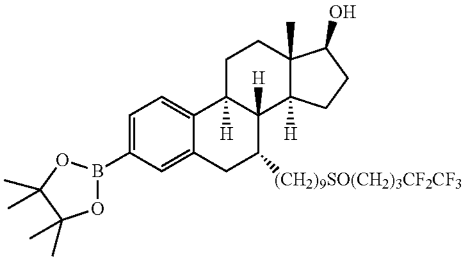

N-1

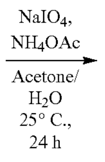

-continued

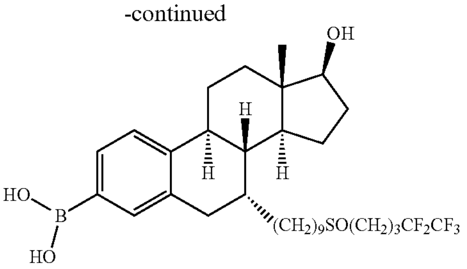

ZB716

A flask is charged with 5 g of intermediate N-1, 55 mL of acetone and 27.5 mL of water. The suspension is kept under stirring at 25° C. for 10 minutes.

5.9 g of sodium periodate and 2.15 g of ammonium acetate are added.

The mixture is kept under stirring at 25° C. for 24 hours (the reaction is monitored by UPLC analysis).

Once the reaction is complete, 75 mL of isopropyl acetate and 65 mL of water are added.

The layers are separated, and the aqueous layer is re-extracted with isopropyl acetate.

The organic layer is washed with a saturated sodium chloride aqueous solution and concentrated under reduced pressure at 45° C. until a solid is obtained.

The product is purified by chromatographic column on silica gel, eluting with a 95:5 methylene chloride/methanol mixture.

The solvent is concentrated under reduced pressure at 45° C. obtaining 2.6 g of the desired compound, ZB716, as a white solid whose $^{1}$H-NMR, $^{13}$C-NMR and Ms analytical data coincide with those reported in the literature.

$^{1}$H-NMR (400 MHz, DMSO-$d_6$): 7.68 (s, 2H); 7.50 (d, 1H, J=7.6 Hz); 7.43 (s, 1H); 7.23 (d, 1H, J=7.6 Hz); 4.36 (d, 1H, J=4.4 Hz); 3.56-3.55 (m, 1H); 2.84-2.60 (m, 6H); 2.45-2.25 (m, 4H); 1.94-1.10 (m, 26H); 0.88 (m, 2H); 0.67 (s, 3H).

The $^{1}$H-NMR signals at 7.68 ppm and 4.36 ppm disappear after deuteration of the sample with $D_2O$.

$^{13}$C-NMR (400 MHz, DMSO-$d_6$): 141.8; 136.4; 134.2; 131.9; 125.3; 80.6; 51.7; 49.9; 46.7; 43.5; 42.1; 39.1; 37.4; 34.7; 33.3; 30.4; 29.8; 29.5; 29.3; 29.1; 29.0; 28.6; 28.0; 27.3; 25.6; 22.8; 22.5; 14.6; 11.8.

Mass (ESI): m/z=657 [$M^{+}$+1+22]; 635 [$M^{+}$+1]; 617 [$M^{+}$+1-$H_2O$].

What is claimed is:

1. A process for the synthesis of B-[(7α,17β)-17-hydroxy-7-[9-[(4,4,5,5,5-pentafluoropentyl)sulfinyl]nonyl]estra-1,3,5(10)-trien-3-yl]-boronic acid (ZB716), comprising the following steps:

a) reaction of intermediate N-3, (7α,17β)-7-[9-[(4,4,5,5,5-pentafluoropentyl)sulfinyl]nonyl]-estra-1,3,5(10)-triene-3,17-diol (Fulvestrant), with a triflating agent to obtain intermediate N-2, (7α,17β)-7-[9-[(4,4,5,5,5-pentafluoropentyl)sulfinyl]nonyl]-estra-1,3,5(10)-triene-3,17-diol-3-triflate:

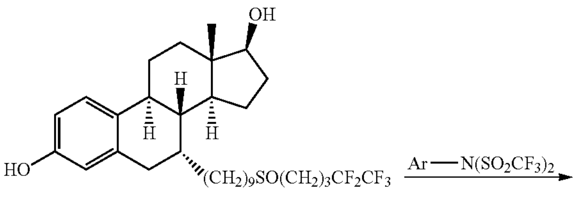

N-3

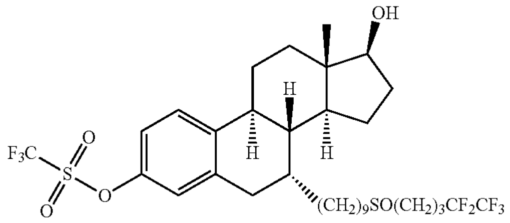

N-2 b) reaction of intermediate N-2 with 4,4,4',4',5,5,5',5'-octamethyl-2,2'-bi-1,3,2-dioxaborolane to obtain intermediate N-1, (7α,17β)-7-[9-[(4,4,5,5,5-pentafluoropentyl)sulfinyl]nonyl]-3-(4,4,5,5-tetramethyl-1,3,2-dioxaborolan-2-yl)-estra-1,3,5(10)-trien-17-ol:

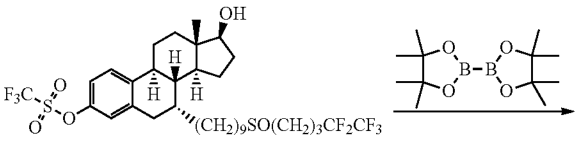

N-2

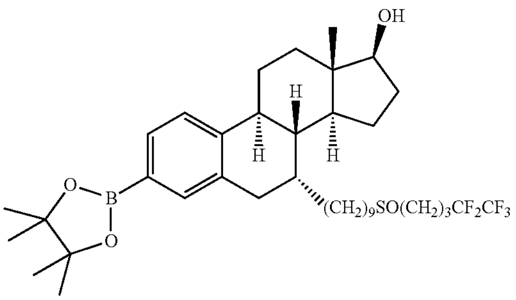

N-1 c) treatment of intermediate N-1 to obtain compound ZB716, B-[(7α,17β)-17-hydroxy-7-[9-[(4,4,5,5,5-pentafluoropentyl)sulfinyl]nonyl]estra-1,3,5(10)-trien-3-yl]-boronic acid:

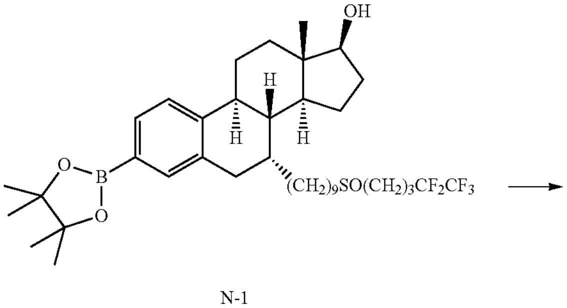

N-1

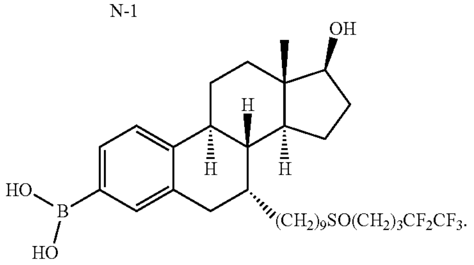

ZB716

2. The process according to claim 1, wherein in step a) an aromatic bis(trifluoromethanesulfonimide) of general formula Ar—N(Tf)$_2$ is used as triflating agent, wherein Ar indicates the aromatic or heterocyclic radical and the N(Tf)$_2$ group is the radical:

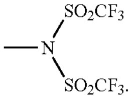

3. The process according to claim 2, wherein said triflating agent is 1,1,1-trifluoro-N-phenyl-N-[(trifluoromethyl)sulfonyl]methanesulfonamide.

4. The process according to claim 1, wherein the reagent used in step c) for the conversion of intermediate N-1 into compound ZB716 is an alkali metal periodate.

5. The process according to claim 4, wherein said reagent is sodium periodate.

6. Compound (7α,17β)-7-[9-[(4,4,5,5,5-pentafluoropentyl)sulfinyl]nonyl]-estra-1,3,5(10)-triene-3,17-diol-3-triflate:

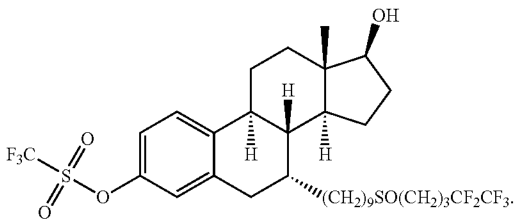

* * * * *